US00PP27656P3

(12) United States Plant Patent
Olesen

(10) Patent No.: US PP27,656 P3
(45) Date of Patent: Feb. 14, 2017

(54) SHRUB ROSE PLANT NAMED 'POULREN023'

(50) Latin Name: ***Rosa* hybrid**
Varietal Denomination: Poulren023

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 187 days.

(21) Appl. No.: 14/121,284

(22) Filed: Aug. 15, 2014

(65) Prior Publication Data
US 2016/0050798 P1 Feb. 18, 2016

(51) Int. Cl.
*A01H 5/02* (2006.01)

(52) U.S. Cl.
USPC ..... Plt./107

(58) Field of Classification Search
USPC ..... Plt./107
See application file for complete search history.

*Primary Examiner* — Keith Robinson

(57) ABSTRACT

A new garden rose plant of the Shrub class which has abundant, light pink flowers and attractive foliage. This new and distinct variety has shown to be uniform and stable in the resulting generations from asexual propagation.

3 Drawing Sheets

Botanical designation: *Rosa* hybrid.
Variety denomination: 'Poulren023'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulren023', originated as a single seedling from the stated cross.

The new variety may be distinguished from its male pollen parent and female seed parent primarily by flower color. The female seed parent and male pollen parent have near white flowers while the new variety has light pink flowers.

The objective of the hybridization of this rose variety was to create a new and distinct variety for garden use with unique qualities, such as:

1. Uniform and abundant light pink flowers with perfume;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulren023' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulren023' was selected in the spring of 2005 by the inventor as a single plant from the progeny of the aforementioned hybridization.

Asexual reproduction of 'Poulren023' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulren023' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren023'.

Specifically illustrated in FIG. 1 are open flowers, flower buds, and flowers in parts.

DETAILED DESCRIPTION OF THE VARIETY

Figure 1:
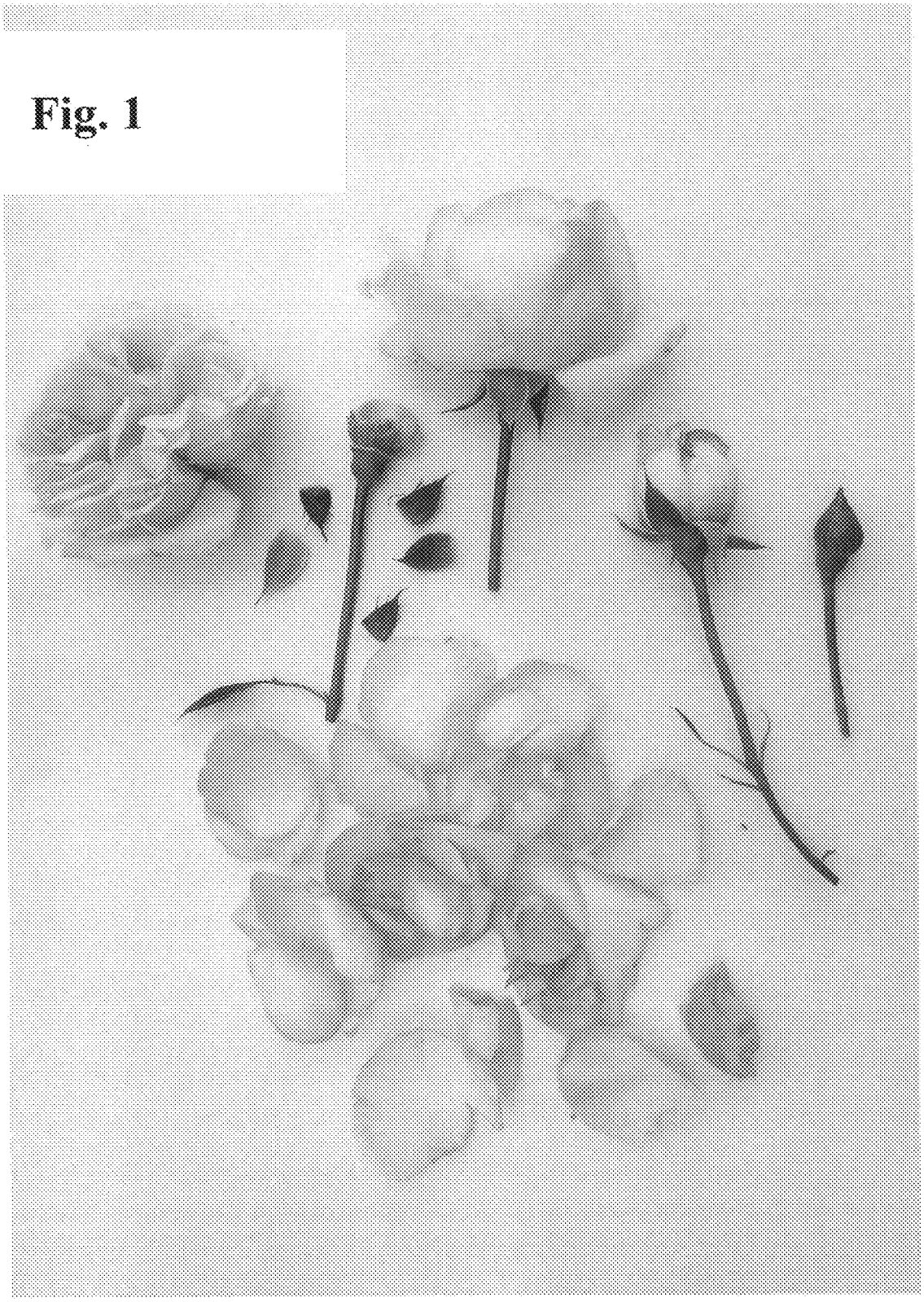
Figure 2:
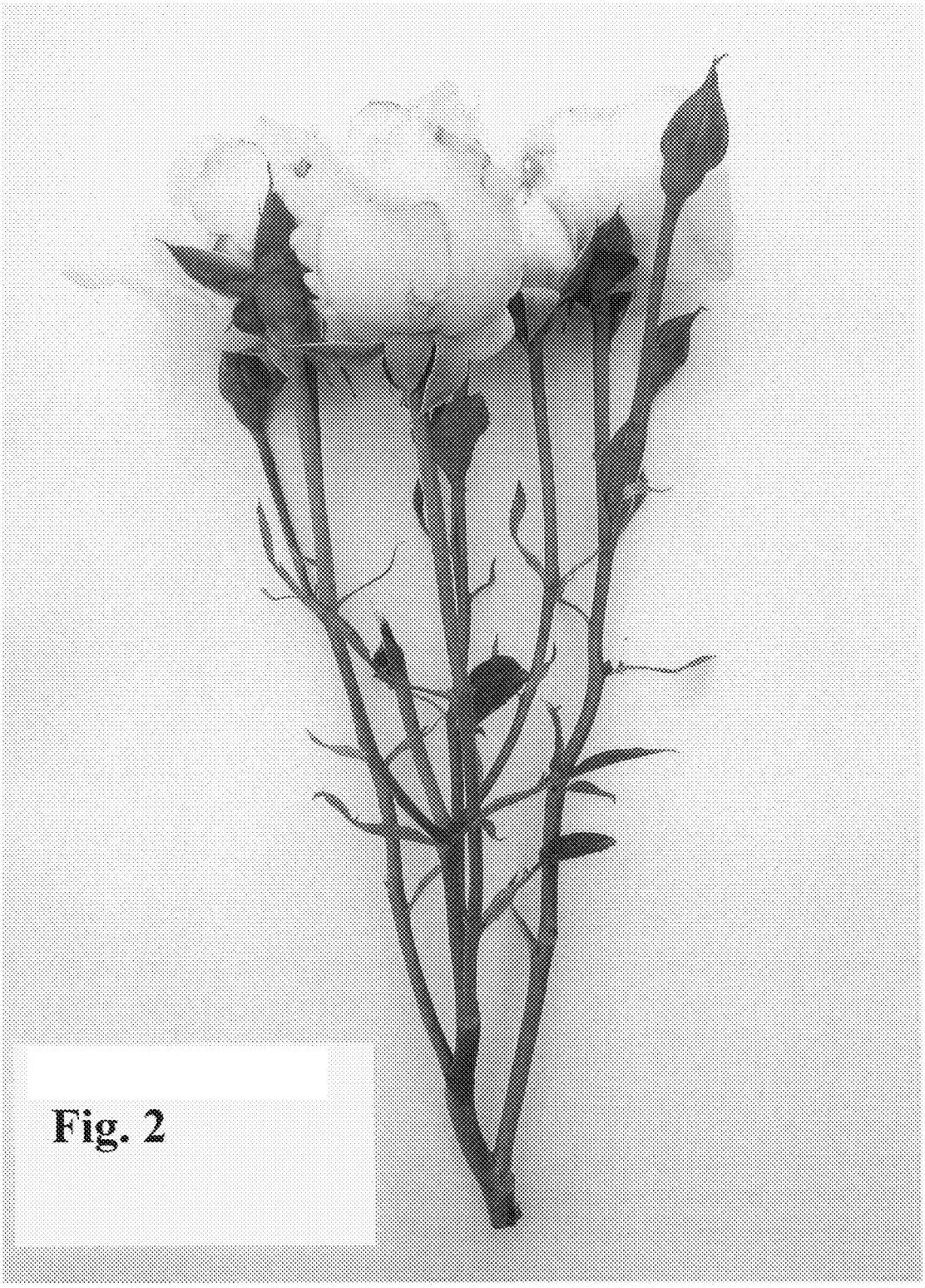
FIG. 2 shows a flowering branch.
Figure 3:
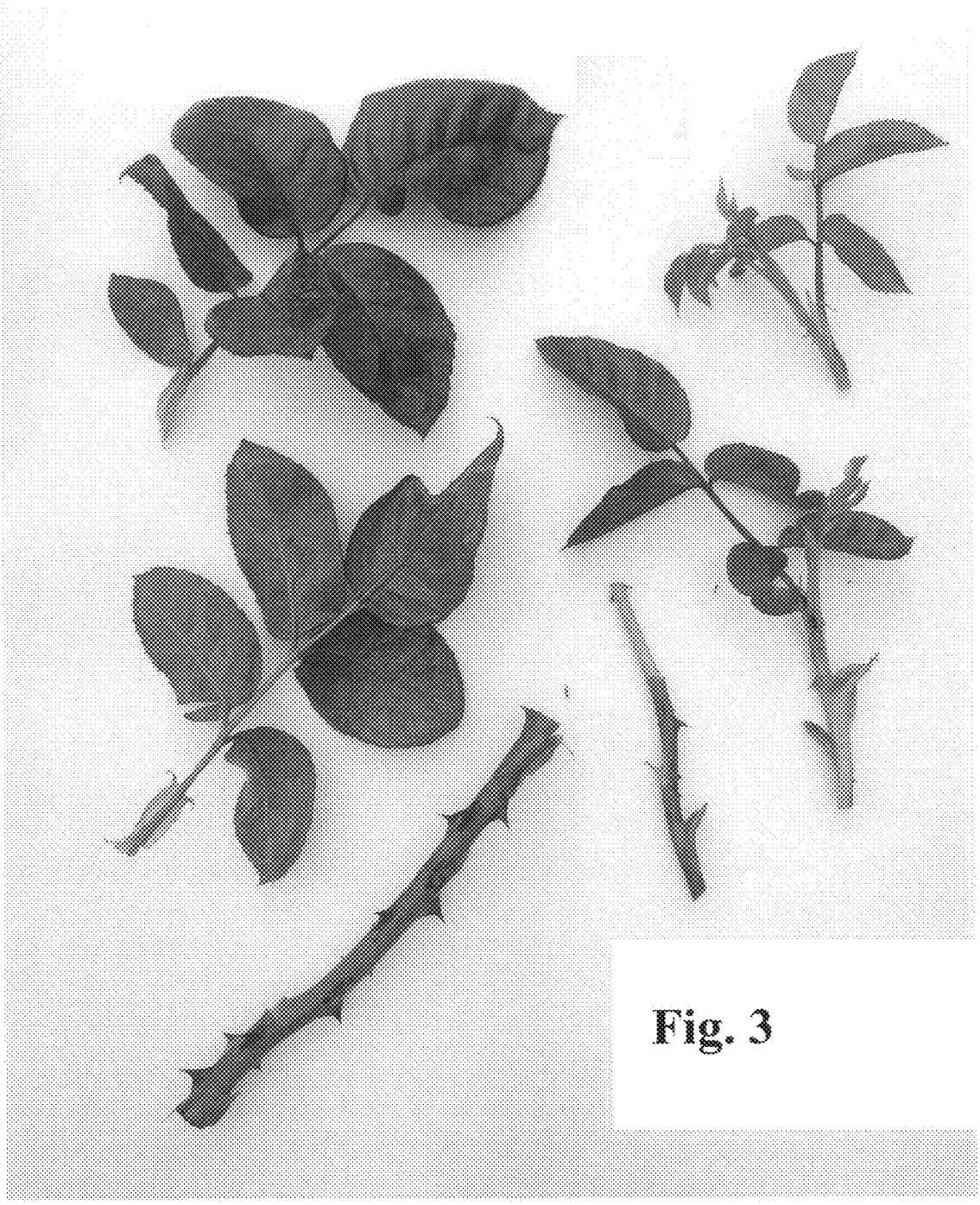
FIG. 3 shows mature leaves, juvenile growth, and stems. Plants shown are 2 years of age.

The following is a description of 'Poulren023', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulht001', described and illustrated in U.S. Plant Pat. No. 15,195 are compared to 'Poulren023' in Chart 1.

CHART 1

| | 'Poulren023' | 'Poulht001' |
|---|---|---|
| Petal Count | 25 to 30 | 25 to 30 |
| Flower Diameter | 105 mm | 80 mm |

CHART 1-continued

| | 'Poulren023' | 'Poulht001' |
|---|---|---|
| Outermost petals, upper surface | Red-Purple Group 69A | White Group 155B with intonations of Red Group 39D |

FLOWER AND FLOWER BUD

Blooming habit: Recurrent.

Flower bud:

*Size.*—Upon opening, 35 mm in length from base of receptacle to end of bud. Bud diameter is 18 mm.

*Bud form.*—Ovoid.

*Bud color.*—As sepals divide petals are Red-Purple Group 69A and White Group N155C with intonations of Red-Purple Group 61B.

*Sepal inner surface.*—Color: Yellow-Green Group 145A with intonations of Greyed-Red Group 182A. Surface: Lightly pubescent.

*Sepal outer surface.*—Color: Yellow-Green Group 144A with strong intonations of Greyed-Purple Group 183A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—30 mm long, 15 mm wide.

*Receptacle.*—Texture: Smooth. Size: 20 mm in height, 20 mm wide. Color: Yellow-Green Group 144A with strong intonations of Greyed-Purple Group 183A. Shape: Campanulate.

*Pedicel.*—Surface: Smooth. Length: About 55 mm. Diameter: 4 mm on average. Color: Yellow-Green Group 144A with intonations of Greyed-Purple Group 185C. Strength: Strong.

Flower bud development: Flower buds are borne in clusters of 3 to 7 flower buds per stem.

Flower bloom:

*Fragrance.*—Very strong perfume.

*Duration.*—The blooms have a duration on the plant of approximately 10 days. Petals fall cleanly away from plant after flowers have fully matured.

*Size.*—Flower diameter is 105 mm when open. Flower depth is 55 mm.

*Flower shape.*—Open rosette, double flower with many slightly overlapping petals of different sizes.

*Shape of flower, side view.*—The upper portion is flat. The lower portion is convex.

Petalage: Under normal conditions, flowers have 25 to 30 petals total, about 3 of which are petaloids.

General tonality of flower: Open flowers are Red Group 49A and Red-Purple Group 62D.

Petal color:

*Upon opening.*—Upper surface: Red Group 49A and 49D. There is a faint petal spot of Yellow Group 4D at the petal base about 5 mm in length. Lower surface: Red Group 49A and Red-Purple Group 62D.

*After opening.*—Upper surface: Red-Purple Group 69A. Inner petals have a petal spot of Yellow Group 4D about 5 mm in length. Lower surface: Red-Purple Group 69A and 69D.

Petals:

*Petal reflex.*—Moderately reflexed.

*Margin.*—Several clefts, and strong undulations.

*Shape.*—Generally broad and rounded. Apex shape: Rounded. Base shape: Rounded.

*Size.*—55 mm (l)×75 mm (w).

*Texture.*—Smooth on both upper and lower surfaces.

*Thickness.*—Above average.

Petaloids:

*Size.*—20 mm (l) by 12 mm (w).

*Quantity.*—About 3.

*Shape.*—Elliptic. Base and apex are acute.

*Color.*—Upper surface: Red-Purple Group 69A. Inner petals have a petal spot of Yellow Group 4D. Lower surface: Red-Purple Group 69A and 69D.

Reproductive organs:

*Pollen.*—None observed.

*Anthers.*—Size: 2 mm in length. Color: Yellow-Orange Group 18C. Quantity: 90 on average.

*Filaments.*—Color: Yellow-Orange Group 20B. Length: 10 mm.

*Pistils.*—Length: 5 mm. Quantity: 35 on average.

*Stigmas.*—Color: Greyed-Yellow Group 160C.

*Styles.*—Color: Red-Purple Group N66B.

*Location of stigmas.*—Inferior in location relative to the length of the filaments and the height of the anthers.

*Hips.*—None Observed.

PLANT

Plant growth: Upright, bushy. Plants are 60 cm in height, and 50 cm wide.

Stems:

*Color.*—Juvenile growth: Yellow-Green Group 144A. Mature growth: Yellow-Green Group 144A.

*Length.*—On average, canes are 45 cm from the base of the plant to the flowering portion.

*Diameter.*—10 mm.

*Internodes.*—On mature canes, there is an average distance of 40 mm between nodes.

*Surface texture.*—Young wood: Smooth. Older wood: Smooth.

Long prickles:

*Incidence.*—7 prickles per 10 cm of stem.

*Size.*—Average length of prickles on mature stems is 5 mm.

*Shape.*—Upper portion is linear. Lower portion is concave.

*Color.*—Juvenile prickles: Greyed-Purple Group 184A. Mature prickles: Greyed-Purple Group 184A.

Plant foliage:

*Compound leaf.*—170 mm (l)×150 (w).

*Quantity.*—2 leaves per 10 cm of stem on average.

*Leaf bearing angle to the stem.*—45 degrees.

*Color of juvenile foliage.*—Upper side: Greyed-Purple Group 187B. Lower side: Greyed-Purple Group 187B.

*Color of mature foliage.*—Upper side: Yellow-Green Group 147A. Lower side: Yellow-Green Group 147B.

Plant leaves and leaflets:

*Stipules.*—Size: 27 mm long, 3 mm wide. Quantity: 2 per compound leaf. Shape: Linear, slightly broad based with outward extending apices. Margins: Finely serrated. Color: Yellow-Green Group 147B.

*Petiole.*—Length: 50 mm. Diameter: 2 mm.

*Upper surface.*—Color: Greyed-Purple Group 187C.

*Lower surface.*—Color: Yellow-Green Group 144B.

*Rachis*.—Length: 20 mm. Upper surface: Color: Yellow-Green Group 147A with strong intonations of Greyed-Purple Group 187B.

*Lower surface*.—Color: Yellow-Green Group 144B. Observations: Small prickles.

*Leaflet*.—Quantity: Normally 5 leaflets. Margins: Serrated. Size: On average terminal leaflets are 75 mm long, 50 mm wide. Shape: Generally elliptical. Base: Rounded. Apex: Cuspidate. Texture: Smooth on both upper and lower surfaces. Thickness: Average. Arrangement: Odd pinnate. Venation: Reticulate. Glossiness: Strong.

Disease resistance: Above average resistance to powdery mildew *Sphaerotheca pannosa*, downy mildew *Peronospora sparsa*, rust *Phragmidium* sps., black spot *Diplocarpon Rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Shrub rose class named 'Poulren023', substantially as illustrated and described herein, due to its abundant light pink flowers, disease resistance, and extended period of bloom.

* * * * *